United States Patent [19]

Fischer

[11] 4,409,183

[45] Oct. 11, 1983

[54] APPARATUS FOR ASCERTAINING THE QUANTITY OF OZONE IN WATER

[76] Inventor: Bertram Fischer, Wolfmadenstrasse 67, D-7000 Stuttgart 80, Fed. Rep. of Germany

[21] Appl. No.: 168,403

[22] Filed: Jul. 10, 1980

[30] Foreign Application Priority Data

Jul. 13, 1979 [DE] Fed. Rep. of Germany ....... 2928324

[51] Int. Cl.³ ..................... G01N 27/26; G01N 27/30
[52] U.S. Cl. ..................................... 422/68; 204/1 T; 204/400; 422/62; 436/135; 436/150
[58] Field of Search ............. 23/230 R, 230 A, 232 E; 422/69, 50; 204/195 R, 1 Y, 1 T; 324/29; 436/135, 150

[56] References Cited

U.S. PATENT DOCUMENTS 3,888,754 6/1975 Tiefenav ......................... 204/195 R
3,960,673 6/1976 Morrow et al. ................ 204/195 R
4,172,015 10/1979 Bamford et al. .................... 204/1 Y

FOREIGN PATENT DOCUMENTS 2719015 1/1980 Fed. Rep. of Germany .

Primary Examiner—Michael S. Marcus
Attorney, Agent, or Firm—Kontler, Grimes & Battersby

[57] ABSTRACT

Apparatus for ascertaining the quantity of ozone in water and for admitting additional ozone when the ascertained quantity is insufficient has two spaced-apart electrodes which consist of an alloy having gold as the predominant constituent thereof and which can be immersed into a body of water. Each electrode is connected with a discrete voltage source by way of a discrete resistor whose resistance is substantially greater than the resistance between the electrodes when the electrodes are immersed in water. The potential difference between the electrodes is measured by a differential amplifier whose output transmits a voltage signal having an intensity proportional to the percentage of ozone in the body of water into which the electrodes are immersed. A signal comparing stage compares the signal at the output of the amplifier with a reference signal denoting the desired quantity of ozone, and the stage transmits a signal to an ozonizer which admits ozone into the body of water when the intensity of signals at the output of the amplifier is less than the intensity of the reference signal.

12 Claims, 2 Drawing Figures

APPARATUS FOR ASCERTAINING THE QUANTITY OF OZONE IN WATER

CROSS-REFERENCE TO RELATED CASE

An apparatus for measuring the quantity of free effective chlorine whose construction is similar to that of the apparatus which embodies the present invention is disclosed in commonly owned German Auslegeschrift No. 2,719,015 of Karl-Heinz Hertneck which was published on Jan. 3, 1980.

BACKGROUND OF THE INVENTION

The present invention relates to a method and apparatus for ascertaining the quantity of ozone in water.

At the present time, the quantity of ozone in water is estimated by resorting to coulometers or by relying on colorimeters. A drawback of conventional techniques is that the apparatus which serve to ascertain the quantity of ozone in water are quite bulky and complex. Therefore, such apparatus cannot be directly coupled with commercial ozonizers in such a way that the quantity of ozone which is admitted by the ozonizer is regulated in automatic response to signals denoting the ascertained quantity of ozone in a water bath or stream to which ozone is to be added in view of its bactericidal qualities and/or for other reasons.

OBJECTS AND SUMMARY OF THE INVENTION

An object of the invention is to provide a novel and improved apparatus for ascertaining the quantity of ozone in a stagnant or flowing body of water with a high degree of accuracy and for any desired period of time.

Another object of the invention is to provide a simple, compact and inexpensive apparatus of the above outlined character which can be directly coupled to one or more ozonizers serving to admit ozone to the body of water wherein the quantity of ozone is monitored.

A further object of the invention is to provide novel and improved water-contacting components for use in an apparatus of the above outlined character.

An additional object of the invention is to provide the apparatus with novel and improved means for evaluating the signals which are furnished by the water-contacting components and for generating signals denoting the ascertained quantity of ozone.

An ancillary object of the invention is to provide a novel and improved connection between the evaluating means and the ozonizer or ozonizers.

Another object of the invention is to provide a novel and improved method of quantitative measurement of ozone in a stagnant or flowing body of water.

One feature of the invention resides in the provision of an apparatus for ascertaining the quantity of ozone in water, e.g., in a body of water which is to constitute or which constitutes a bactericidal or sterilizing bath. The apparatus comprises spaced-apart water-immersible first and second electrodes each of which consists of an alloy wherein the predominant metal is gold (for example, the alloy may consist of 80 percent by weight of gold, 15 percent by weight of silver, 3 percent by weight of palladium and 2 percent by weight of platinum). Furthermore, the apparatus comprises first and second means for establishing a constant flow of electric current through each of the electrodes at an amperage between 0.1 and 1 microampere. The flow establishing means includes means for applying to the electrodes a voltage of identical absolute value but of opposite polarity.

In accordance with a presently preferred embodiment, the flow establishing means comprises first and second resistor means which are respectively connected in series with the first and second electrodes. The resistance of each of these resistor means can be in the range of between 20 and 50 megohms and is greater than the resistance between the two electrodes. The flow establishing means preferably further comprises first and second energy sources and conductor means which connect the first and second energy sources with the respective electrodes; the aforementioned resistors are installed in the corresponding conductor means. The potential difference between the electrodes is continuously measured by a differential amplifier constituting a means for evaluating the signal or signals which are generated by the electrodes; the output of the amplifier transmits signals which denote (or are proportitonal to) the quantity of ozone in the body of water in which the electrodes are immersed.

Another feature of the invention resides in the provision of a method of ascertaining the quantity of ozone in a body of water. The method comprises the steps of inserting into the body of water two spaced-apart electrodes consisting of an alloy wherein gold is the predominant metal, establishing a constant flow of electric current through each of the electrodes at an amperage of 0.1–1 microampere, and generating signals denoting the potential difference between the electrodes. Such signals are proportional to the quantity of ozone in the body of water and can be utilized to denote such quantity (e.g., by resorting to a gauge or another suitable instrument) or to automatically regulate the admission of ozone to the body of water so that the monitored quantity matches a preselected optimum value.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

DESCRIPTION OF THE PREFERRED EMBODIMENTS

Figure 1:
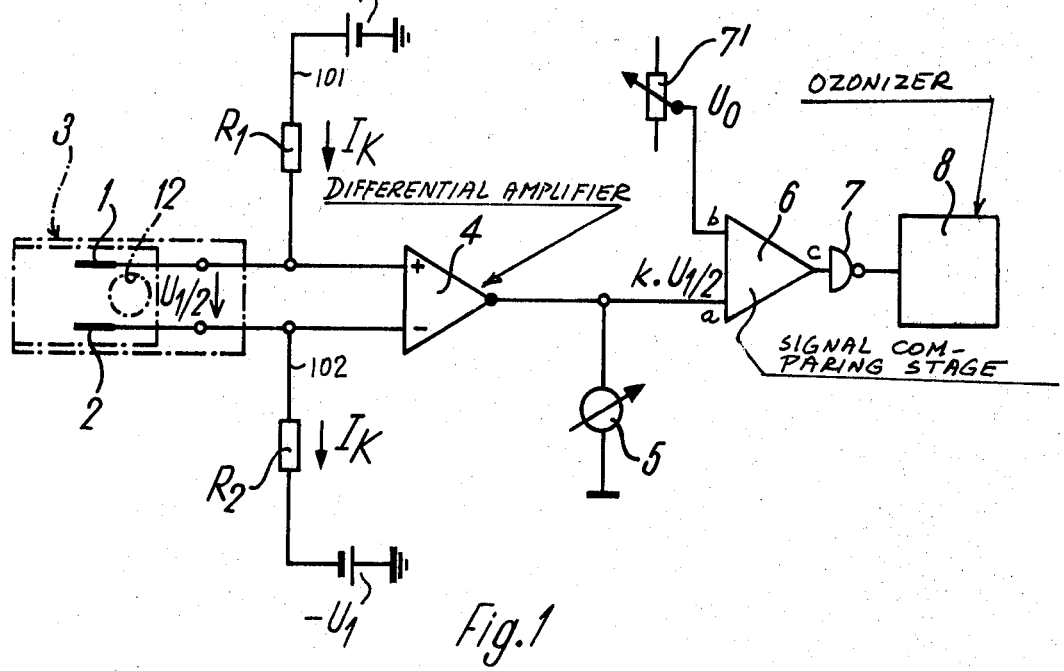
FIG. 1 is a diagrammatic view of an apparatus which serves to ascertain the quantity of ozone in a body of water and is constructed and assembled in accordance with an embodiment of the present invention.

The apparatus which is shown schematically in FIG. 1 comprises a cell 3 with two spaced-apart electrodes 1 and 2. For example, a portion of the housing 13 (see FIG. 2) of the cell 3 can be immersed into a body of water in a tank or basin, or into a stream of water in a pipe 50 constituting the outlet of a tank or the like. The purpose of the apparatus is to ascertain the quantity of ozone in the flowing stream (or in a stagnant body) of water and to indicate the monitored quantity of ozone (see the gauge 5) and/or to activate an ozonizer (shown schematically at 8) whenever the monitored quantity of ozone is less than a desirable optimum quantity. Thus, the quantity of ozone in the body of water can be automatically maintained at or very close to a given value.

The means for establishing a constant flow of electric current through the electrodes 1 and 2 comprises first and second energy sources U1 and −U1 and conductor means 101, 102 which connect the electrodes 1, 2 with the respective energy sources and contain resistors R1 and R2, respectively. It will be noted that the resistors R1 and R2 are connected in series with the corresponding electrodes 1 and 2. The source U1 applies to the electrode 1 a positive voltage (U1), and the source −U1 applies to the electrode 2 a negative voltage (−U1) of identical absolute value, i.e., only the polarities of the voltages which are applied to the electrodes 1 and 2 are different. The resistance $R_M$ between the electrodes 1 and 2 (when such electrodes are immersed in a body of water) is a relatively small fraction of the resistance of the resistor R1 or R2. For example, the resistance $R_M$ may be in the range of between 2.5 and 9 megohms if the resistance of the resistor R1 or R2 is between 20 and 50 megohms. The potential difference U1 or −U1 may be in the range of 5 volts. The resistance of the resistors R1 and R2 is selected in such a way that a constant current $I_K$ is impressed upon the electrodes 1 and 2, namely, a current which is constant irrespective of eventual fluctuations of conductivity of the body of water in the space between the electrodes 1 and 2. This can be achieved, for example, by selecting the resistances of the resistors R1 and R2 in such a way that their sum is very much larger than the resistance $R_M$ between the electrodes 1 and 2. Also, the resistance of each of the resistors R1 and R2 is preferably greater than $R_M$ as already mentioned. If the resistance of the resistor R1 matches that of the resistor R2 and is approximately 40 megohms, the impressed current $I_K$ is approximately 0.12 microampere.

The distance between the electrodes 1 and 2 may be in the range of 10 millimeters.

It has been found, quite surprisingly, that fluctuations of the quantity of ozone in the body of water in which the electrodes 1 and 2 are immersed entails corresponding or proportional fluctuations of the potential difference $U_{\frac{1}{2}}$ between the electrodes. This potential difference (which is symmetrical with reference to the zero point in view of the identical absolute magnitudes of voltages which are applied to the electrodes 1 and 2) is measured by an evaluating means including a differential amplifier 4 whose positive and negative inputs are respectively connected with the electrodes 1 and 2. The (first) signals at the output of the amplifier 4 are indicative of the quantity of ozone in the body of water into which the electrodes 1 and 2 extend. The input resistance of the differential amplifier 4 is preferably very high; suitable differential amplifiers of such character are available on the market. The amplitude of the (first) signals at the output of the differential amplifier 4 equals $kU_{\frac{1}{2}}$, i.e., it is proportional to the potential difference $U_{\frac{1}{2}}$ and is measured by a suitable gauge or other instrument 5 of any known design. The gauge 5 is preferably calibrated in such a way that its pointer can indicate the monitored quantity of ozone in the body of water.

If the apparatus is intended for automatic regulation of the quantity of ozone in a body of water into which the electrodes 1 and 2 are immersed, the gauge 5 is replaced by or is used simultaneously with an arrangement which is shown in the right-hand portion of FIG. 1 and includes a suitable ozonizer 8 capable of generating ozone at a variable rate and/or of admitting ozone at a variable rate into the aforementioned body of water. The arrangement comprises a signal comparing stage 6 having a first input a for the (first) signals which are transmitted by the output of the differential amplifier 4, a second input b for reference signals $U_0$ which are transmitted by a suitable source 7' of reference signals (e.g., an adjustable potentiometer), and an output c which transmits signals to an inverter 7, the latter being connected with the input of the ozonizer 8. The reference signal $U_0$ is a voltage signal, the same as the signal $kU_{\frac{1}{2}}$ at the input a of the signal comparing stage 6. The signal at the output c of the stage 6 is proportional to the difference ($U_{\frac{1}{2}}$-$U_0$) of the intensities of the signals which are transmitted to the inputs a and b. The reference signal $U_0$ is an adjustable optimum or threshold value of the signal $kU_{\frac{1}{2}}$ which corresponds to the actual content of ozone in the monitored body of water. When the intensity of the signal $kU_{\frac{1}{2}}$ drops below the intensity of the signal $U_0$, the output c of the stage 6 transmits a signal to the inverter 7 which actuates the ozonizer 8. The latter admits a larger quantity of ozone into the body of water whereby the intensity of the signal $kU_{\frac{1}{2}}$ increases, i.e., the difference in the intensities of the signals at the inputs of the stage 6 decreases. When such difference decreases to zero, the body of water contains the desired quantity of ozone and the ozonizer 8 is arrested or continues to supply ozone at the rate which is needed to maintain the quantity of ozone at the optimum value.

Owing to the fact that the potentials which are applied to the electrodes 1 and 2 are identical but of opposite polarity, any disturbances which would be attributable to synchronization as well as any disturbances which could cause a shifting of potentials at the electrodes 1 and 2 with reference to the zero point are eliminated in a simple and efficient way. This applies particularly for potentials which develop as a result of ionization of water in the cell 3 or of the influence of substances which are contained in water. Furthermore, since one operates with impressed current, it is possible to eliminate all influences which could develop as a result of a change in the resistance at the transition regions between the measuring electrodes and the body of water. For example, the resistance at the transition regions may change due to galvanizing of the electrodes. The aforediscussed relationship between resistances renders it possible to insure that the dissociation currents and/or voltages which develop as a result of such currents cannot cause any, or cannot cause appreciable, distortion of the results of the measurements.

Another important advantage of the improved apparatus is that it operates with a surprisingly low current. This is believed to be the main reason that the improved apparatus is capable of furnishing reliable indications of the quantity of ozone and/or of effecting reliable regulation of the rate of admission of ozone into the body of water for extended periods of time. It would appear that a relatively low current fails to induce any, or induces negligible, electrochemical reactions in the cell 3, i.e., reactions of an intensity which could lead to distortion of the signals indicated by the pointer and scale of the gauge 5 and/or could influence the operation of the ozonizer 8.

Figure 2:
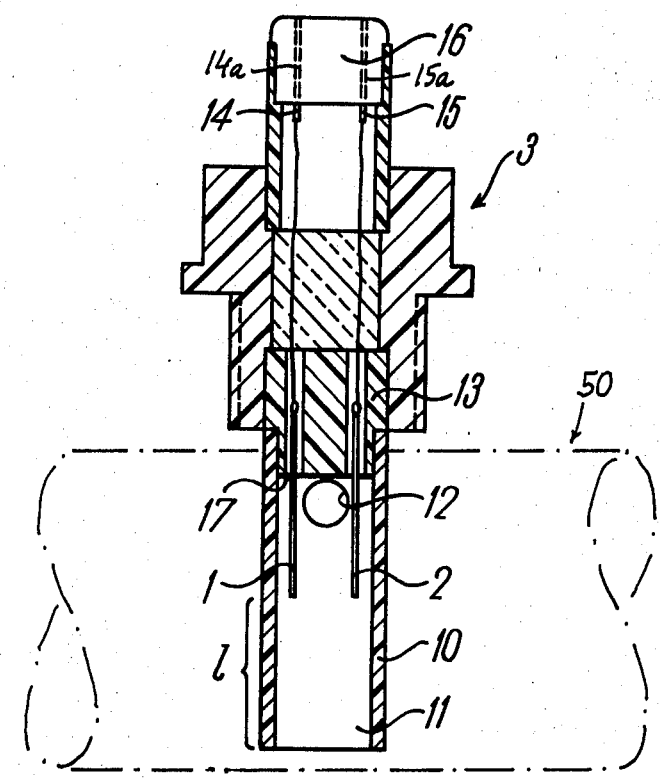
FIG. 2 is an enlarged central sectional view of a cell which includes the electrodes of the improved apparatus and at least a portion of which is immersible into a stagnant or flowing body of water so as to permit the water to contact the electrodes.

FIG. 2 illustrates a presently preferred embodiment of the cell 3. The electrodes 1 and 2 are installed in the interior of a tubular portion or sleeve 10 of the housing 13 of the cell 3. The sleeve 10 consists of electrically insulating material and the open end of the cylindrical chamber 11 which is defined by the sleeve 10 is located at a distance l of 10-20 millimeters from the tips of the electrodes 1 and 2. The inner end portion of the chamber 11 communicates with the body of water into which the electrodes 1 and 2 are immersed by way of one or more openings 12 (only one shown in each of FIGS. 1 and 2). The electrodes 1 and 2 extend through the inner portion of the body or housing 13 and are connected with terminals 14 and 15 which, in turn, are connectable with complementary terminals 14a and 15a of a plug 16 which is removably insertable into the rear end portion of the housing 13.

It is desirable to provide a discrete insulating layer 17 at the inner end of the chamber 11 within the sleeve 10 so as to ensure a highly reliable insulating effect. The opening or openings 12 are adjacent to the insulating layer 17 (this layer is applied to that portion of the housing 13 which carries the sleeve 10) and ensure that the water which contacts the electrodes 1 and 2 in the interior of the sleeve 10 is in continuous contact with the major portion of the body of water. This reduces the likelihood of generation of spatial charges in the chamber 11 which, in turn, further guarantees a high reproducibility and long-lasting reliability of indications which are furnished by the improved apparatus and denote the quantity of ozone in the body of water.

It has been found that the operation of the cell 3 is particularly satisfactory if the material of the electrodes 1 and 2 is an alloy which contains predominantly gold. For example, a highly satisfactory alloy is one which contains 80 percent by weight of gold, 15 percent of silver, 3 percent of palladium and 2 percent of platinum. Such an alloy contributes significantly to reliability of the measurements. Moreover, it has been found that electrodes which consist of such an alloy prevent an increase in the potential difference between the electrodes even in the event that the body of water contains (organic and/or inorganic) substances which tend to enhance the conductivity of the liquid. The exact cause for such advantageous properties of electrodes having the above composition is not known at this time. However, it is believed that the composition of the alloy is an important factor which contributes to desirable characteristics of the cell 3 having the aforediscussed electrodes 1 and 2, especially the presence of platinum and/or gold in the alloy. Electrodes consisting of an alloy including gold and platinum have been found to be superior to electrodes which are made of pure gold.

Electrodes which consist of pure gold and conduct relatively small currents are known from the art of monitoring fluids for the presence of other substances, e.g., for ascertaining the quantity of free effective chlorine. Reference may be had to the aforementioned commonly owned German Auslegeschrift No. 2,719,015. However, the effectiveness of cells with electrodes which consist predominantly of gold for measurement of ozone in a body of water was not known before and is believed to be highly surprising, especially in view of the high degree of accuracy and reproducibility of the measuring or monitoring operation as well as in view of the high degree of accuracy during monitoring for extended periods of time. The improved method is believed to be the first method which can be resorted to in connection with commercially available ozonizers for automatic regulation of the admission of ozone to bodies of water which constitute bactericidal baths or baths having other beneficial properties.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. Apparatus for use in ascertaining the quantity of ozone in water, comprising spaced-apart water-immersible first and second electrodes each of which consists of an alloy the predominant metal of which is gold; means for establishing through each of said electrodes a constant flow of electric current in the range of 0.1 to 1 microampere, including means for applying to said electrodes voltages of identical absolute value but opposite polarity; means for measuring the potential difference between said electrodes, including a differential amplifier having output means for the transmission of first signals denoting the measured potential difference; means connecting said measuring means with said electrodes; a source of reference signals denoting a voltage which is indicative of an acceptable quantity of ozone in the water; means for comparing the signals from said amplifier and said source, said comparing means having first and second inputs, and an output arranged to transmit signals denoting the difference between the characteristics of signals received at said first and second inputs; ozonizer means arranged to supply ozone to the water at a rate which is a function of the characteristics of signals at said output of said comparing means; means connecting said output means of said amplifier with said first input; means connecting said source with said second input; and means connecting said output of said comparing means with said ozonizer means.

2. The apparatus of claim 1, wherein said flow establishing means comprises first and second resistor means respectively connected in series with said first and second electrodes, the resistance of each of said resistor means being greater than the resistance between said electrodes when the electrodes are immersed in a body of water.

3. The apparatus of claim 1, further comprising inverter means connected between said ozonizer means and said output of said signal comparing means.

4. The apparatus of claim 1, wherein said source of reference signals includes means for furnishing reference signals of different intensities.

5. The apparatus of claim 1, wherein said ozonizer means is constructed and assembled to supply ozone to the body of water into which said electrodes are immersed in response to transmission thereto of a signal which is generated by said signal comparing means when the intensity of said reference signals exceeds the intensity of said first signals.

6. The apparatus of claim 1, wherein the distance between said electrodes is approximately 10 millimeters.

7. The apparatus of claim 1, wherein said alloy further contains platinum.

8. The apparatus of claim 1, wherein said alloy is 80 percent by weight of gold, 15 percent by weight of silver, 3 percent by weight of palladium and 2 percent by weight of platinum.

9. The apparatus of claim 1, wherein said flow establishing means comprises first and second energy sources, and additional means for connecting said first and second sources with the respective electrodes, said additional connecting means including first and second resistors.

10. The apparatus of claim 9, wherein the resistance of each of said resistors is in the range between 20 and 50 megohms.

11. The apparatus of claim 1, further comprising a housing for said electrodes, said housing including a tubular portion surrounding said electrodes and having an open end remote from said electrodes and at least one opening nearer to said electrodes than said open end, said opening and said open end permitting circulation of water along said electrodes when said tubular portion is immersed into a body of water.

12. The apparatus of claim 11, wherein said flow establishing means comprises first electric terminals installed in said housing and connected with said electrodes, sources of electrical energy, and second electric terminals connected with said energy sources and connectable with said first terminals.

* * * * *